(12) United States Patent
Suzuki et al.

(10) Patent No.: US 10,209,189 B2
(45) Date of Patent: *Feb. 19, 2019

(54) SPECTRUM MEASURING DEVICE, SPECTRUM MEASURING METHOD, AND SPECIMEN CONTAINER

(71) Applicant: HAMAMATSU PHOTONICS K.K., Hamamatsu-shi, Shizuoka (JP)

(72) Inventors: Kengo Suzuki, Hamamatsu (JP); Kazuya Iguchi, Hamamatsu (JP); Shigeru Eura, Hamamatsu (JP); Kenichiro Ikemura, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 10 days.

This patent is subject to a terminal disclaimer.

(21) Appl. No.: 14/764,703

(22) PCT Filed: Sep. 17, 2013

(86) PCT No.: PCT/JP2013/075033
§ 371 (c)(1),
(2) Date: Jul. 30, 2015

(87) PCT Pub. No.: WO2014/119038
PCT Pub. Date: Aug. 7, 2014

(65) Prior Publication Data
US 2015/0346096 A1    Dec. 3, 2015

(30) Foreign Application Priority Data

Feb. 4, 2013  (JP) ................................ 2013-019409

(51) Int. Cl.
*G01N 21/64* (2006.01)
*G01N 21/01* (2006.01)
(Continued)

(52) U.S. Cl.
CPC ............ *G01N 21/645* (2013.01); *G01J 3/021* (2013.01); *G01J 3/0254* (2013.01); *G01J 3/0291* (2013.01);
(Continued)

(58) Field of Classification Search
CPC ...... G01J 3/0254; G01J 3/0291; G01J 3/4406; G01N 21/645; G01N 21/01
See application file for complete search history.

(56) References Cited

U.S. PATENT DOCUMENTS 4,583,860 A     4/1986  Butner
4,765,718 A *   8/1988  Henkes ............. G02F 1/133524
                                                    349/57

(Continued)

FOREIGN PATENT DOCUMENTS

CN    101627288    1/2010
CN    102066910    5/2011
(Continued)

OTHER PUBLICATIONS

N. Greenham et al., "Measurement of absolute photoluminescence quantum efficiencies in conjugated polymers," Chemical Physics Letters, vol. 241, Issues 1-2, Jul. 14, 1995, pp. 89-96.

(Continued)

*Primary Examiner* — Michael C Bryant
(74) *Attorney, Agent, or Firm* — Drinker Biddle & Reath LLP

(57) ABSTRACT

A spectral measurement apparatus for irradiating a sample as a measurement object with excitation light and detecting light to be measured includes a light source generating the excitation light; an integrator having an input opening portion through which the excitation light is input, and an output opening portion from which the light to be measured is output; a housing portion arranged in the integrator and
(Continued)

housing the sample; an incidence optical system making the excitation light incident to the sample; a photodetector detecting the light to be measured output from the output opening portion; and an analysis device calculating a quantum yield of the sample, based on a detection value detected by the photodetector, and the excitation light is applied to the sample so as to include the sample.

8 Claims, 11 Drawing Sheets

(51) Int. Cl.
  *G01J 3/44* (2006.01)
  *G01J 3/02* (2006.01)
(52) U.S. Cl.
  CPC .......... *G01J 3/4406* (2013.01); *G01N 21/01* (2013.01); *G01N 21/6489* (2013.01); *G01N 2021/6469* (2013.01); *G01N 2021/6482* (2013.01); *G01N 2021/6484* (2013.01); *G01N 2201/065* (2013.01)

(56) References Cited

U.S. PATENT DOCUMENTS

| | | | | |
|---|---|---|---|---|
| 5,623,342 | A * | 4/1997 | Baldwin | G01J 3/44 356/301 |
| 5,859,709 | A | 1/1999 | Imura | |
| 7,952,071 | B2 * | 5/2011 | Noji | H01J 37/045 250/307 |
| 9,423,339 | B2 * | 8/2016 | Eura | G01J 3/4406 |
| 2005/0002037 | A1 * | 1/2005 | Harrison | G01J 3/2803 356/445 |
| 2010/0108869 | A1 * | 5/2010 | Iguchi | G01J 1/02 250/228 |
| 2011/0031410 | A1 | 2/2011 | Tanaami et al. | |
| 2011/0255085 | A1 * | 10/2011 | Watanabe | G01J 3/02 356/317 |
| 2015/0377770 | A1 * | 12/2015 | Eura | G01J 3/4406 356/402 |
| 2017/0153142 | A1 * | 6/2017 | Rosen | G01J 3/0275 |

FOREIGN PATENT DOCUMENTS

| | | |
|---|---|---|
| CN | 102187203 | 9/2011 |
| EP | 2 124 028 | 11/2009 |
| EP | 2 261 641 | 12/2010 |
| JP | H06-8526 Y2 | 3/1994 |
| JP | 2003-215041 A | 7/2003 |
| JP | 2004-309323 A | 11/2004 |
| JP | 2007-086031 A | 4/2007 |
| JP | 2009-103654 A | 5/2009 |
| JP | 3165429 U | 1/2011 |
| JP | 2011-027755 | 2/2011 |
| JP | 2011-196735 A | 10/2011 |
| JP | 2013-011617 | 1/2013 |
| KR | 10-2010-0014765 | 2/2010 |
| TW | 201224437 | 6/2012 |
| WO | WO 2009/050536 | 4/2009 |
| WO | WO 2011/148079 | 12/2011 |
| WO | WO-2012/073567 A1 | 6/2012 |

OTHER PUBLICATIONS

J. de Mello et al., "An Improved Experimental Determination of External Photoluminescence Quantum Efficiency," Advanced Materials, vol. 9, Issue 3, 1997, pp. 230-232.

Y. Ichino, "Theoretical Analysis of Integrating Sphere-based Absolute Photoluminescence Quantum Efficiency Measurement," The 71$^{st}$ Japan Society of Applied Physics Meeting, 14p-NK-6, 2010, with English language translation.

L. Porres, "Absolute Measurements of Photoluminescence Quantum Yields of Solutions Using an Integrating Sphere", Journal of Fluorescence, Feb. 14, 2006, pp. 267-273.

* cited by examiner

Fig.9
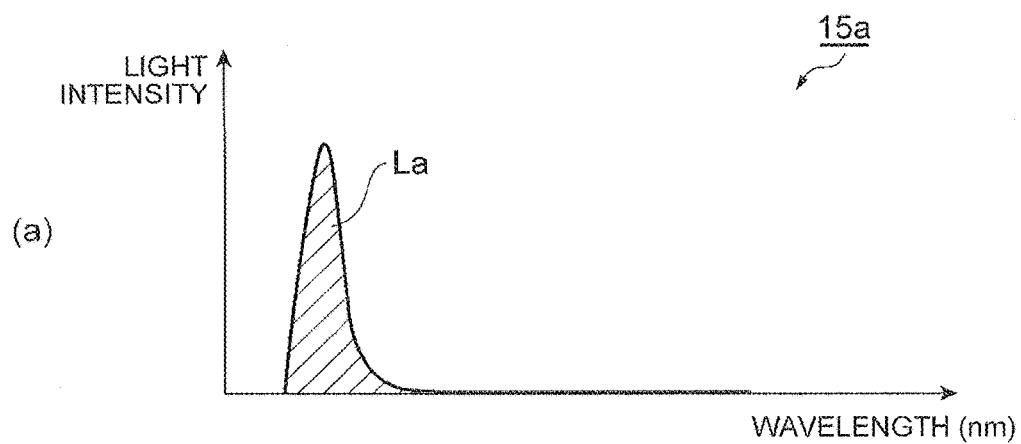
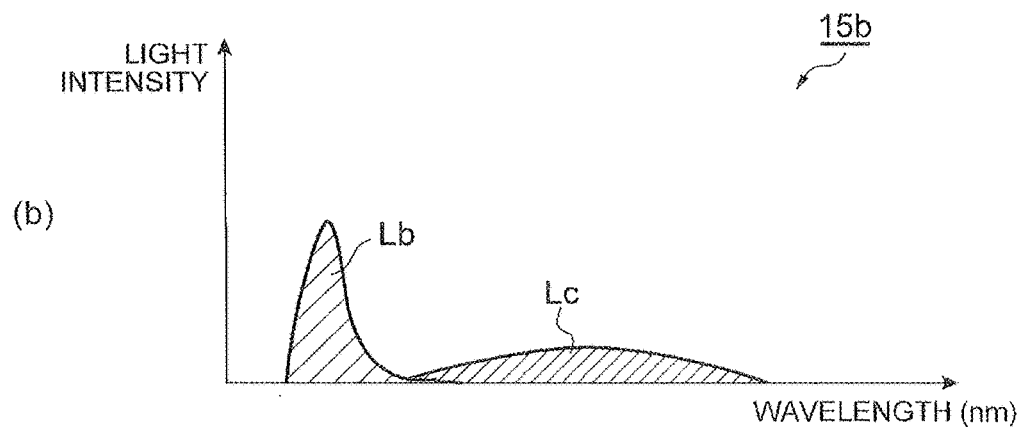

SPECTRUM MEASURING DEVICE, SPECTRUM MEASURING METHOD, AND SPECIMEN CONTAINER

TECHNICAL FIELD

The present invention relates to a spectral measurement apparatus, a spectral measurement method, and a sample container.

BACKGROUND ART

There is a conventionally-known spectral measurement apparatus configured to irradiate a sample as a measurement object with excitation light and detect light to be measured, and as a technology of this kind, for example, Patent Document 1 describes the quantum efficiency measurement apparatus. The quantum efficiency measurement apparatus described in this Patent Document 1 is configured to integrate reflection components from a fluorescent substance of single-wavelength radiation and all radiation components of excited fluorescence emission by an integrating sphere to measure a spectral energy distribution thereof, and to integrate all reflection components from a spectral reflectance standard of single-wavelength radiation by the integrating sphere to measure a spectral distribution thereof. Then the apparatus calculates the number of photons absorbed by the fluorescent substance and the number of photons of the fluorescence emission, based on the measurement values, and calculates a quantum yield of the fluorescent substance from a ratio of these numbers.

Furthermore, for example, Patent Document 2 describes the absolute fluorescence quantum efficiency measurement apparatus configured as follows; in obtaining a quantum yield, the sample is fixed at a position where the sample is not directly hit by the excitation light in the integrating sphere, and the absorptance of the sample is obtained from an intensity obtained with indirect incidence of the excitation light to the sample and an intensity obtained with direct incidence of the excitation light to the sample. Non Patent Documents 1 to 3 describe calculation of quantum yields on the premise that the excitation light is made incident to a part of the sample.

CITATION LIST

Patent Literature

Patent Document 1: Japanese Patent Application Laid-Open No. 2003-215041
Patent Document 2: Japanese Patent Application Laid-Open No. 2011-196735

Non Patent Literature

Non Patent Document 1: "Measurement of absolute photoluminescence quantum efficiencies in conjugated polymers Chemical Physics Letters Volume 241", Issues 1-2, 14 Jul. 1995, Pages 89-96, N. C. Greenham, I. D. W. Samuel, G. R. Hayes, R. T. Phillips, Y. A. R. R. Kessener, S. C. Moratti, A. B. Holmes, R. H. Friend Non Patent Document 2: "An improved experimental determination of external photoluminescence quantum efficiency Advanced Materials", Vol. 9, Issue 3, March 1997, Pages 230-232, John C. de Mello, H. Felix Wittmann, Richard H. Friend Non Patent Document 3: "Theoretic study on absolute fluorescence quantum efficiency measurement method using integrating sphere", The 71st JSAP Meeting (Sep. 12, 2010), 14p-NK-6, Yoshiro ICHINO (2010.9.12) 14p-NK-6

SUMMARY OF INVENTION

Technical Problem

Here, in general, when a sample is excited, light to be measured (fluorescence) is radiated into all directions. Since many samples have an absorption wavelength region also including the light to be measured, they bring about self-absorption such that the sample itself absorbs the light to be measured emitted by itself. In this respect, since a quantum yield is expressed by a ratio of the number of photons of the excitation light absorbed by the sample, to the number of photons of the light to be measured, the calculated quantum yield might be estimated smaller than a true value if the light to be measured is absorbed by the self-absorption.

Therefore, one aspect of the present invention is directed to a problem to provide a spectral measurement apparatus, a spectral measurement method, and a sample container capable of accurately determining the quantum yield.

Solution to Problem

In order to solve the above problem, a spectral measurement apparatus according to one aspect of the present invention is a spectral measurement apparatus for irradiating a sample as a measurement object with excitation light and detecting light to be measured, comprising: a light source which generates the excitation light; an integrator having an input opening portion through which the excitation light is input, and an output opening portion from which the light to be measured is output; a housing portion which is arranged in the integrator and which houses the sample; an incidence optical system which makes the excitation light incident to the sample; a photodetector which detects the light to be measured output from the output opening portion; and analysis means which calculates a quantum yield of the sample, based on a detection value detected by the photodetector, wherein the excitation light is applied to the sample so as to include the sample.

The spectral measurement apparatus according to the one aspect of the present invention can reduce the self-absorption amount and thus has made it feasible to accurately determine the quantum yield. The reason for it is as follows. Namely, when the excitation light is applied to a part of the sample, the self-absorption amount is large because of a wide boundary area between an irradiated region and a non-irradiated region in the sample; whereas the spectral measurement apparatus according to the one aspect of the present invention is configured to apply the excitation light so that the excitation light includes the sample; and, for this reason, the boundary area between the irradiated region and non-irradiated region in the sample becomes narrower, so as to reduce the self-absorption amount.

A specific example of a configuration for suitably achieving the foregoing operational effect is a configuration wherein the incidence optical system adjusts the excitation light so that the excitation light includes the sample. Another example is a configuration wherein the housing portion houses the sample so that the excitation light includes the sample.

The integrator may have a sample introduction opening portion to which a sample holder for arranging the housing portion in the integrator is attached, and the sample holder may be attached to the sample introduction opening portion so that an opening plane of the housing portion is inclined relative to an orthogonal plane to an irradiation optical axis of the excitation light. In this case, reflected light of the excitation light can be prevented from returning directly to the input opening.

An inclination direction of the opening plane of the housing portion and a long axis direction of the opening plane of the housing portion may be identical to each other. The incidence optical system may comprise an optical member having an opening of a shape having a long axis, and there may be an angle between a long axis direction of the opening of the optical member and the inclination direction of the opening plane of the housing portion. In these cases, the irradiation shape with the excitation light becomes longitudinally longer, whereby the excitation light can include the housing portion with certainty.

The sample holder may have a mount surface for a sample container including the housing portion to be mounted thereon, and may be attached to the sample introduction opening portion so that the mount surface is inclined relative to the orthogonal plane to the irradiation optical axis of the excitation light. In this regard, the sample holder may comprise an inclined member having the mount surface. Furthermore, the incidence optical system may have an optical member for adjusting an angle of the irradiation optical axis to the opening plane of the housing portion.

A spectral measurement method according to one aspect of the present invention is a spectral measurement method for irradiating a sample as a measurement object with excitation light and detecting light to be measured, comprising: a step of arranging the sample in an integrator; a step of applying the excitation light into the integrator to make the excitation light incident to the sample so that the excitation light includes the sample; a step of detecting the light to be measured output from the integrator; and a step of calculating a quantum yield of the sample, based on the detected light to be measured.

This spectral measurement method also achieves the foregoing operational effect of reducing the self-absorption amount of the light to be measured by the sample, and accurately determining the quantum yield.

A sample container according to one aspect of the present invention is a sample container to be used in quantum yield measurement using an integrator, comprising: a plate portion of a rectangular plate shape; a projected portion disposed on the plate portion; and a housing portion disposed in the projected portion and configured to house a sample as a measurement object, wherein the housing portion houses the sample so that excitation light applied to the sample includes the sample.

This sample container also achieves the foregoing operational effect of reducing the self-absorption amount of the light to be measured by the sample, and accurately determining the quantum yield.

Here, a cross section of the projected portion may be circular, and an opening of the housing portion may be of a shape having a long axis. The foregoing sample container is preferably one formed by fixing a cylindrical member with a through hole onto a surface of a plate-shaped member, wherein the plate portion is configured by the plate-shaped member, the projected portion is configured by the cylindrical member, and the housing portion is configured by the through hole, and in this case, the sample container can be manufactured relatively easily.

Advantageous Effects of Invention

The one aspect of the present invention has made it feasible to accurately determine the quantum yield.

BRIEF DESCRIPTION OF DRAWINGS

FIG. 9 includes (a) a graph showing an example of a wavelength spectrum detected in reference measurement, and (b) a graph showing an example of a wavelength spectrum detected in sample measurement.

DESCRIPTION OF EMBODIMENTS

A preferred embodiment will be described below in detail with reference to the drawings. In the below description, identical or equivalent elements will be denoted by the same reference symbols; without redundant description.

Figure 1:
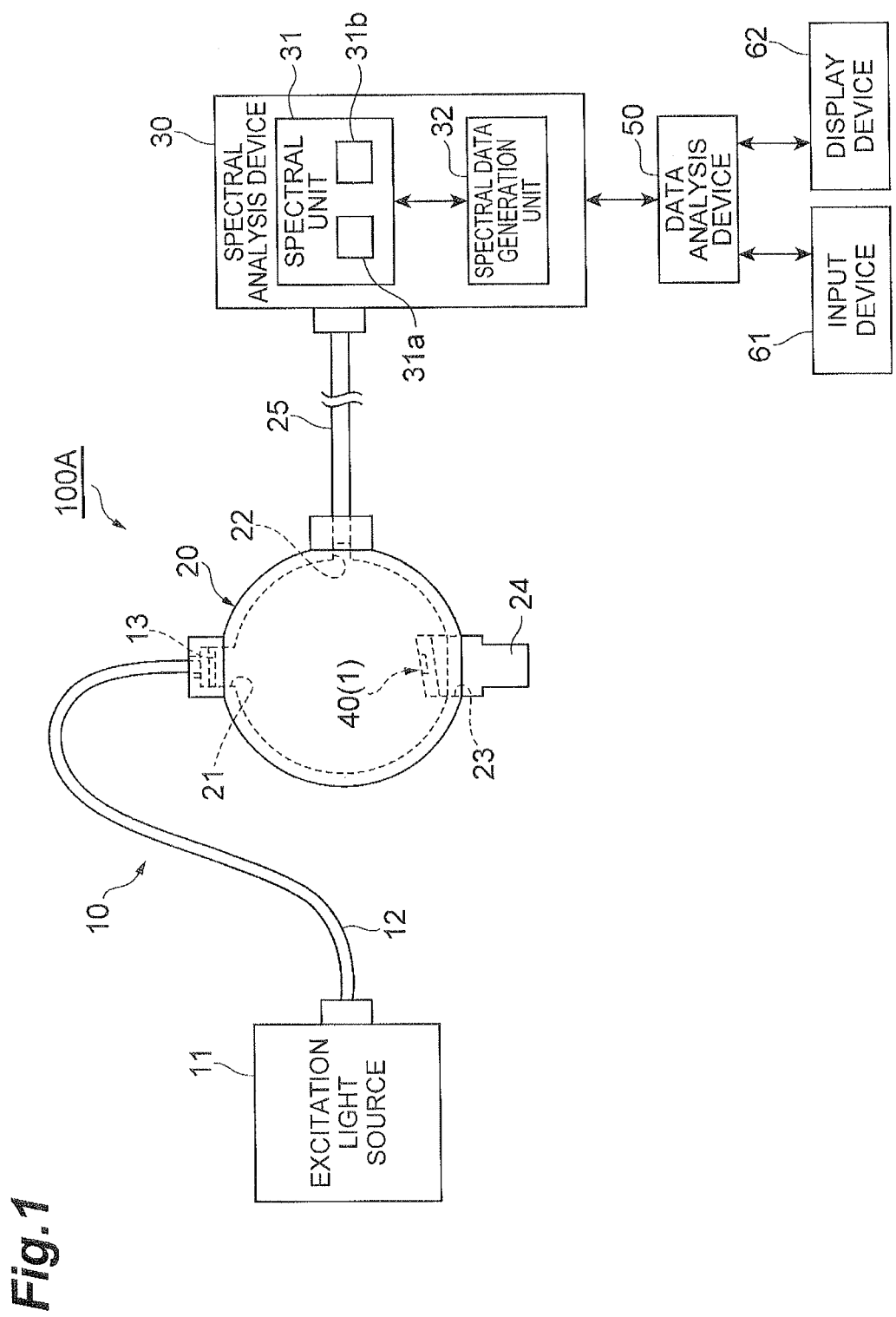
FIG. 1 is a perspective view showing a spectral measurement apparatus according to an embodiment.

FIG. 1 is a drawing schematically showing a configuration of a spectral measurement apparatus according to an embodiment. As shown in FIG. 1, the spectral measurement apparatus 100A according to the present embodiment is an apparatus that measures or evaluates luminescence characteristics such as fluorescence characteristics by the photoluminescence method (PL method), for a sample 1 as a sample to be a measurement object. The sample 1 can be, for example, one of organic EL (Electroluminescence) materials and fluorescent materials such as luminescence materials for white LED (Light Emitting Diode), for FPD (Flat Panel Display), and so on and it can be, for example, of a form such as a powder form, a liquid form (solution form), a solid form, or a thin film form.

The spectral measurement apparatus 100A is configured to irradiate the sample 1 with excitation light of a predetermined wavelength and detect light to be measured generated in response to the irradiation. This spectral measurement apparatus 100A has an excitation light supply unit 10, an integrating sphere (integrator) 20, a spectral analysis device 30, and a data analysis device 50. The excitation light supply unit 10 is a unit for applying the excitation light for measurement of luminescence characteristics to the sample 1. The excitation light supply unit 10 is configured including at least an excitation light source (light source) 11, an input light guide 12, and an optical filter 13.

The excitation light source 11 is a part that generates the excitation light, and is configured, for example, by a xenon lamp, a spectroscope, and so on. The input light guide 12 is a part that guides the excitation light generated by the excitation light source 11 to the integrating sphere 20, and, for example, an optical fiber can be used as the input light guide 12. The optical filter 13 selects a predetermined wavelength component from the light from the excitation light source 11 and outputs the excitation light of the predetermined wavelength component. An interference filter or the like is used as the optical filter 13.

The integrating sphere 20 has an input opening portion 21 for input of the excitation light into the integrating sphere 20, an output opening portion 22 for output of the light to be measured to the outside, and a sample introduction opening portion 23 for introduction of the sample 1 into the interior of the integrating sphere 20. A sample container holder (sample holder) 24 is attached (or fixed) to the sample introduction opening portion 23 and a sample container 40 housing the sample 1 is mounted to be held on the sample container holder 24 in the integrating sphere 20.

An output end of the input light guide 12 is fixed to the input opening portion 21 and the optical filter 13 is installed on the front side in an irradiation direction of the excitation light for the input light guide 12. On the other hand, an input end of an output light guide 25 for guiding the light to be measured to the subsequent spectral analysis device 30 is fixed to the output opening portion 22. For example, a single fiber or a bundled fiber can be used as the output light guide 25.

The spectral analysis device 30 disperses the light to be measured output from the output opening portion 22 of the integrating sphere 20 and guided through the output light guide 25, to acquire a wavelength spectrum thereof. The spectral analysis device 30 herein is configured as a multi-channel spectroscope having a spectral unit 31 and a spectral data generation unit 32.

The spectral unit 31 is configured by a spectroscope 31a for decomposing the light to be measured into wavelength components, and a photodetector 31b for detecting the light to be measured decomposed by the spectroscope 31a. For example, a CCD linear sensor in which pixels of multiple channels (e.g., 1024 channels) for detection of the respective wavelength components of the light to be measured are one-dimensionally arrayed can be used as the photodetector 31b. A measurement wavelength region by the spectral unit 31 can be properly set according to a specific configuration, usage, and so on.

The spectral data generation unit 32 performs signal processing necessary for detection signals output from the respective channels of the photodetector 31b, to generate data of a wavelength spectrum being spectral data of the light to be measured. The data of the wavelength spectrum generated by this spectral data generation unit 32 is output to the subsequent data analysis device 50.

The data analysis device 50 is an analysis means that performs a data analysis necessary for the wavelength spectrum generated by the spectral analysis device 30, to acquire information about the sample 1. The data analysis device 50 herein calculates the quantum yield of the sample 1, based on the output from the spectral analysis device 30 (details of which will be described below).

Connected to the data analysis device 50 are an input device 61 used for input of instructions for the data analysis and others, or for input of analysis conditions, and so on, and a display device 62 used for display of the obtained data analysis result and others.

Figure 2:
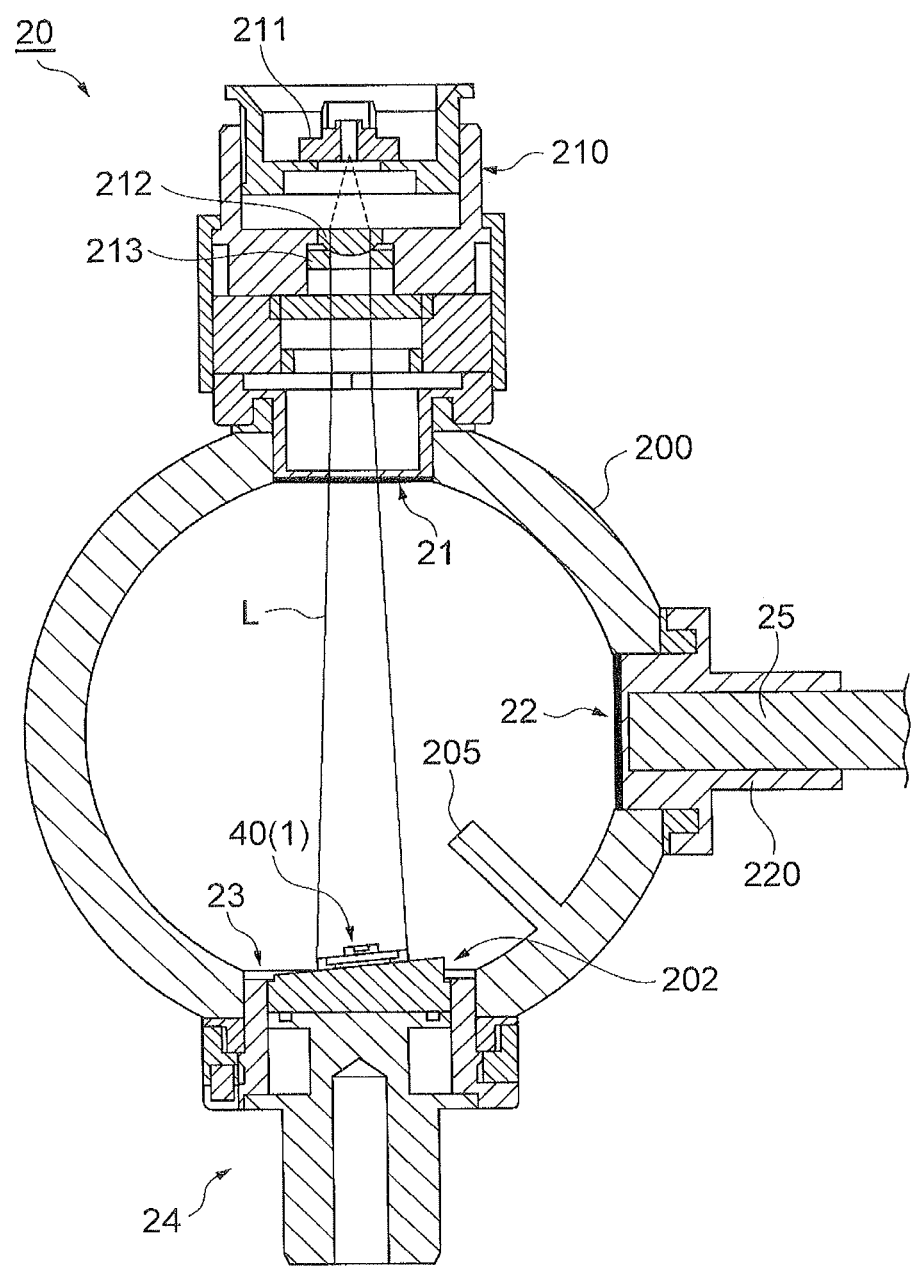
FIG. 2 is a cross-sectional view showing an example of an integrating sphere in the spectral measurement apparatus in FIG. 1.

FIG. 2 is a cross-sectional view showing an example of the integrating sphere in the spectral measurement apparatus in FIG. 1. As shown in FIG. 2, the integrating sphere 20 is attached, for example, to a mount (not shown) with fixing screws or the like, and an inner wall thereof is coated with a high diffuse reflection material. The integrating sphere 20 has an integrating sphere main body 200 and the integrating sphere main body 200 is provided with the aforementioned input opening portion 21, output opening portion 22, and sample introduction opening portion 23.

The input opening portion 21 is provided on the upper side of the integrating sphere main body 200 which is the upstream side of the irradiation optical axis of the excitation light L (hereinafter referred to simply as "irradiation optical axis"). An input light guide holder 210 for connecting the input light guide 12 (cf. FIG. 1) to the integrating sphere main body 200 is inserted and attached to this input opening portion 21.

Figure 5:
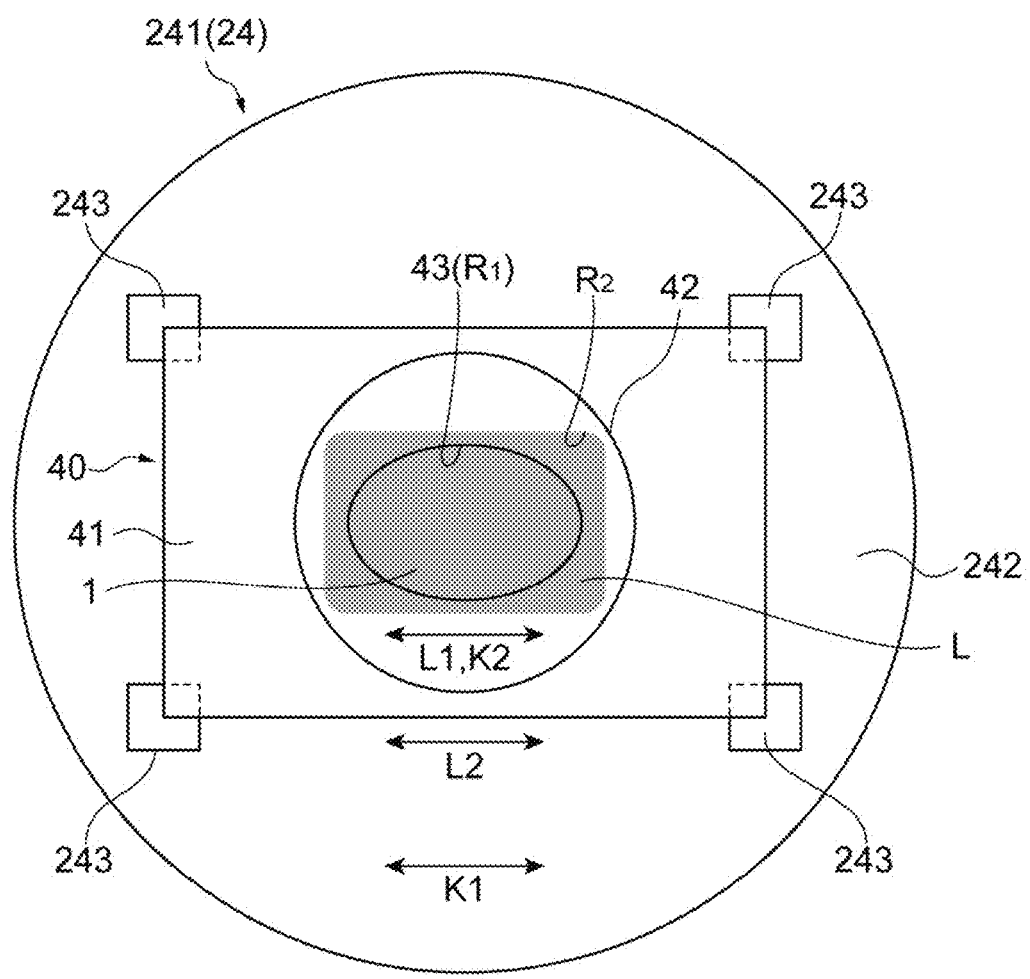
FIG. 5 is a plan view of the sample container holder viewed from a mount surface side.

The input light guide holder 210 has a light guide holding portion 211 for holding the output light guide 25 in position. The input light guide holder 210 is provided with a collimator lens 212 and an aperture (optical member) 213 which are arranged in this order from the upstream to the downstream on the irradiation optical axis. The collimator lens 212 and the aperture 213 constitute an incidence optical system for making the excitation light L incident to the sample 1 and optically adjust the excitation light L so that it can propagate while expanding in the integrating sphere 20. Specifically, the collimator lens 212 and the aperture 213 apply the excitation light L with a predetermined divergence angle such that an irradiation area $S_2$ with the excitation light L is set larger than an irradiated area $S_1$ of the sample 1, as shown in FIG. 5. Here, the excitation light L is applied to the sample 1 so as to include the sample 1.

The irradiated area $S_1$ of the sample 1 is an area of an irradiated region $R_1$ irradiated with the excitation light L in the sample 1, and the irradiation area $S_2$ with the excitation light L is an area of an irradiation region $R_2$ with the excitation light L at a position of incidence to the sample 1. The irradiation region $R_2$ with the excitation light L has a rectangular shape (e.g., a rectangle) on a top plan view (when viewed from the irradiation direction of the excitation light L), and is set so that the length thereof along the long axis direction at the position of incidence to the sample 1 is, for example, about 8 mm.

Referring back to FIG. 2, the output opening portion 22 is provided at a predetermined position on a plane passing a central position of the integrating sphere main body 200 and being perpendicular to the irradiation optical axis. A light guide holder 220 for connecting the output light guide 25 to the integrating sphere main body 200 is inserted and attached to the output opening portion 22.

The sample introduction opening portion 23 is provided so as to face the input opening portion 21, on the lower side of the integrating sphere main body 200. The sample container holder 24 for the sample container 40 to be arranged in the integrating sphere 20 is inserted and detachably attached to the sample introduction opening portion 23.

A light shield plate 205 projecting into the interior of the integrating sphere main body 200 is provided at a predetermined position between the sample introduction opening portion 23 and the output opening portion 22 on the inner wall surface of the integrating sphere main body 200. The light shield plate 205 prevents fluorescence from the sample 1 from directly entering the output light guide 25.

Figure 3:
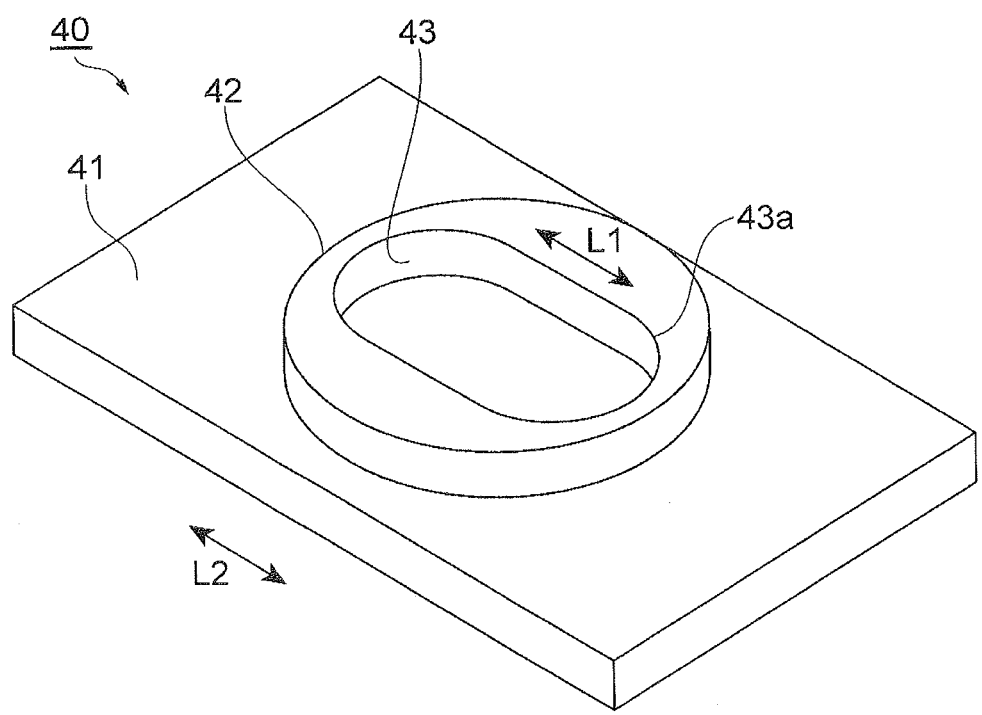
FIG. 3 is a perspective view showing an example of a sample container in the spectral measurement apparatus in FIG. 1.
Figure 4:
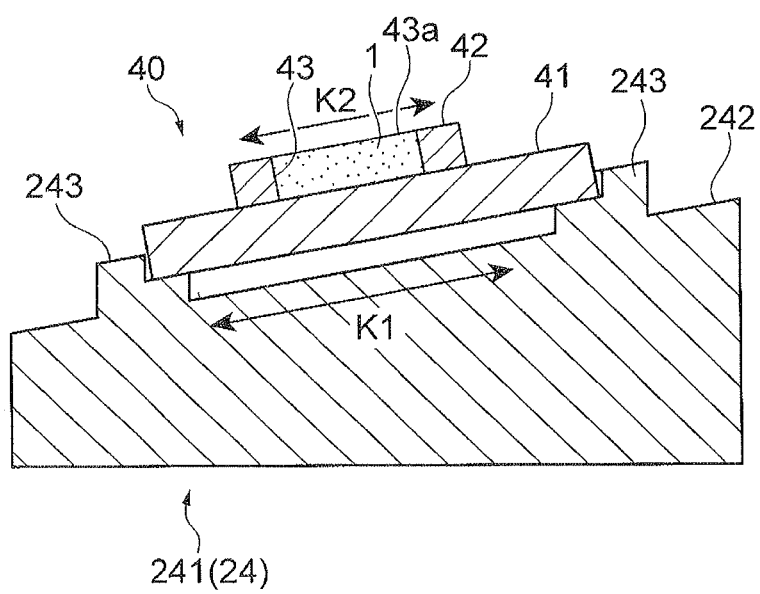
FIG. 4 is a cross-sectional view showing an example of a sample container holder in the spectral measurement apparatus in FIG. 1.

FIG. 3 is a perspective view showing an example of the sample container in the spectral measurement apparatus in FIG. 1, FIG. 4 a cross-sectional view showing an example of the sample container holder in the spectral measurement apparatus in FIG. 1, and FIG. 5 a plan view of the sample container holder in FIG. 4 viewed from the mount surface side. As shown in FIG. 3, the sample container 40 is a container that is used in quantum yield measurement and the like making use of the integrating sphere 20, and has a flange portion (plate portion) 41 of a rectangular plate shape (e.g., a rectangle), a projected portion 42 provided on the flange portion 41, and a housing portion 43 provided in the projected portion 42 and serving as a depressed portion for housing the sample 1.

The shape of the flange portion 41 does not have to be limited to the rectangular shape but may be another shape such as a circular shape or an elliptical shape. The sample container 40 of this configuration can be manufactured by fixing a cylindrical member with a through hole in its central part onto a plate member (plate-shaped member) by adhesion or the like. By this, a portion of the plate member where the cylindrical member is not bonded becomes the flange portion 41, and the through hole of the cylindrical member becomes the housing portion 43 as a depressed portion for housing the sample 1. This manufacturing method allows us to relatively easily manufacture the sample container 40.

This sample container 40 is made, for example, of a transparent material such as quartz or synthetic quartz because it is favorable for purposes including suppression of absorption of light by the sample container 40. It is noted that the sample container 40 does not have to be perfectly transparent. The projected portion 42 has a circular outer shape when viewed from top and its cross section is circular. The housing portion 43, when viewed from top, has an oblong shape elongated in the longitudinal direction of the flange portion 41 (which is, in other words, a track shape having the same long axis as the flange portion 41). Namely, a long axis direction L1 of a plane defined by an opening of the housing portion 43 (hereinafter referred to as opening plane 43a of the housing portion 43) is identical to a long axis direction L2 of the flange portion 41. The shape of the opening plane 43a of the housing portion 43 does not have to be limited to the oblong shape, but may be any shape having a long axis, such as a rectangular shape or an elliptical shape. Since the opening plane 43a of the housing portion 43 has the shape having the long axis, the opening area can be made larger. This housing portion 43 can house the sample 1 so that the excitation light L to be applied to the sample 1 includes the sample 1 (cf. FIG. 5).

As shown in FIGS. 4 and 5, the sample container holder 24 is a part that holds the sample container 40 in the integrating sphere 20. A portion of the sample container holder 24 to be introduced into the integrating sphere 20 is coated with the same high diffuse reflection material as the inner wall of the integrating sphere 20 is. This sample container holder 24 has a mount table (inclined member) 241 and the mount table 241 has a mount surface 242 on which the sample container 40 is to be mounted. The mount surface 242 is formed so that it becomes inclined relative to the perpendicular plane (orthogonal plane) to the irradiation optical axis, when the sample container holder 24 is attached to the sample introduction opening portion 23. Therefore, the opening plane 43a of the housing portion 43 can be made inclined relative to the orthogonal plane to the irradiation optical axis, by attaching the sample container holder 24 to the sample introduction opening portion 23 of the integrating sphere 20. Positioning portions 243 as projected portions protruding upward are formed at locations near the outer periphery on this mount surface 242.

The positioning portions 243 are located at four positions with intervals corresponding to the outer shape of the flange portion 41 of the sample container 40. These positioning portions 243 have a rectangular prism shape an inside top corner of which is cut away. By arranging the sample container 40 so as to be fitted in the inside defined by such four positioning portions 243, the flange portion 41 of the sample container 40 becomes engaged with each positioning portion 243, whereby the sample container 40 is held as positioned on the mount table 241. The positioning portions 243 herein position the sample container 40 so that the long axis direction of the housing portion 43 in the sample container 40 thus arranged is identical to the long axis direction of the irradiation region $R_2$ with the excitation light L. At this time, since the sample container is positioned so that the inclination direction of the mount table 241 is also identical to the long axis direction of the housing portion 43 in the arranged sample container 40, the inclination direction and the long axis direction of the housing portion 43 become identical to each other.

Figure 6:
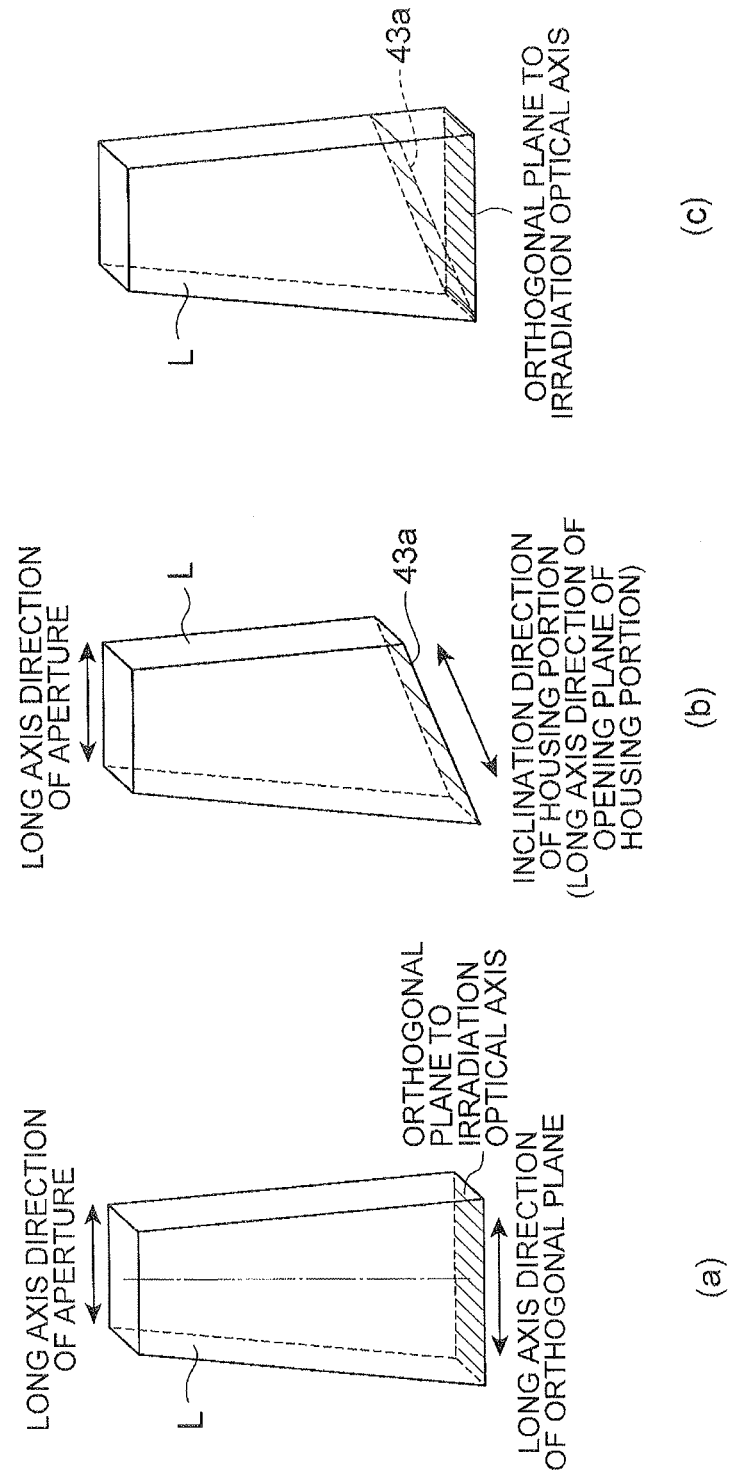
FIG. 6 is a drawing illustrating a relationship between an aperture and a housing portion.

FIG. 6 is a drawing illustrating the relationship between the aperture and the housing portion. With use of FIG. 6, the following will describe the relationship between the long axis direction of the aforementioned aperture 213 and the inclination direction of the housing portion 43 (the long axis direction of the opening plane 43a of the housing portion 43), and the effect thereof. As shown in (a) and (c) in FIG. 6, the excitation light L is shaped into the shape having the long axis (e.g., a rectangular shape) by the opening of the aperture 213 and then it propagates while expanding in the integrating sphere 20. Therefore, the orthogonal plane to the irradiation optical axis of the excitation light L has the shape having the long axis and the long axis direction of the aperture 213 becomes identical to the orthogonal plane of the irradiation optical axis, in contrast to it, as shown in (b) and (c) in FIG. 6, the inclination of the mount table 241 makes the opening plane 43a of the housing portion 43 of the sample container 40 inclined relative to the orthogonal plane to the irradiation optical axis and the inclination direction of the opening plane 43a of the housing portion 43 of the sample container 40 becomes identical to the long axis direction of the opening plane 43a (that is, the long axis direction of the opening of the aperture 213 intersects at an angle with the inclination direction (or, the long axis direction) of the opening plane 43a of the housing portion 43). Therefore, the irradiation region of the excitation light L becomes longitudinally longer than the shape after shaped by the aperture 213, and thus becomes more likely to include the housing portion 43 of the sample container 40.

Figure 7:
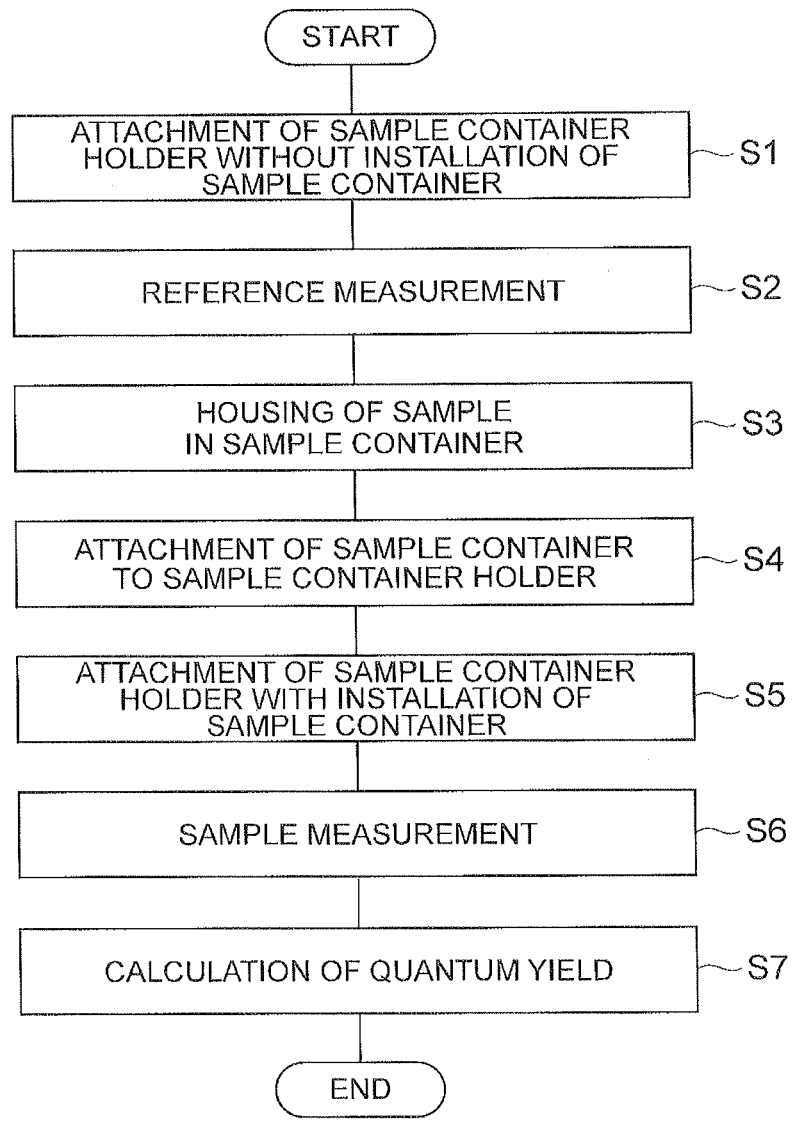
FIG. 7 is a flowchart showing a spectral measurement method using the spectral measurement apparatus in FIG. 1.

Next, a spectral measurement method by the foregoing spectral measurement apparatus 100A will be described with reference to the flowchart of FIG. 7.

First, the sample container holder 24 without installation of the sample container 40 (i.e., in the absence of the sample 1) is attached to the sample introduction opening portion 23 (S1). In this state, the sample container holder 24 functions as a part of the inner wall of the integrating sphere 20. Then, reference measurement is performed which is spectral measurement in a state in which the sample 1 is not arranged in the integrating sphere 20 (S2).

Specifically, the light is emitted from the excitation light source 11 and the excitation light L is guided through the input light guide 12 to be input from the input opening portion 21 into the integrating sphere 20. Then the light to be measured, after multiple diffuse reflections inside the integrating sphere 20, is guided from the output opening portion 22 through the output light guide 125 to the spectral analysis device 30 and the spectral analysis device 30 acquires a wavelength spectrum 15*a* (cf. (a) in FIG. 9). Since this wavelength spectrum 15*a* has the intensity in the excitation wavelength region, the data analysis device 50 integrates the intensity in the excitation wavelength region to acquire an excitation light region intensity La.

Next, the sample 1 is housed in the sample container 40 (S3). Namely, as shown in (a) in FIG. 8, a housing aid cover 45 of a circular ring plate shape is attached to the sample container 40. Specifically, while the projected portion 42 is inserted to be fitted in an opening 46 of a shape according to the cross-sectional outer shape of the projected portion 42 in the housing aid cover 45, the housing aid cover 45 is mounted on the flange portion 41 to cover the top side of the flange portion 41. The housing aid cover 45 has the thickness approximately equal to or smaller than that of the projected portion 42. Furthermore, the sample 1 often has a color such as yellow, and thus the housing aid cover 45 is black in color because it is favorable for grasping the position of the sample 1.

The shape of the housing aid cover 45 is not limited to the circular ring plate shape but the shape of the opening 46 is preferably circular. When the outer peripheral shape of the projected portion 42 of the sample container 40 to be fitted in the opening 46 is circular, it becomes easier to implement handling such as engagement with use of tweezers.

Figure 8:
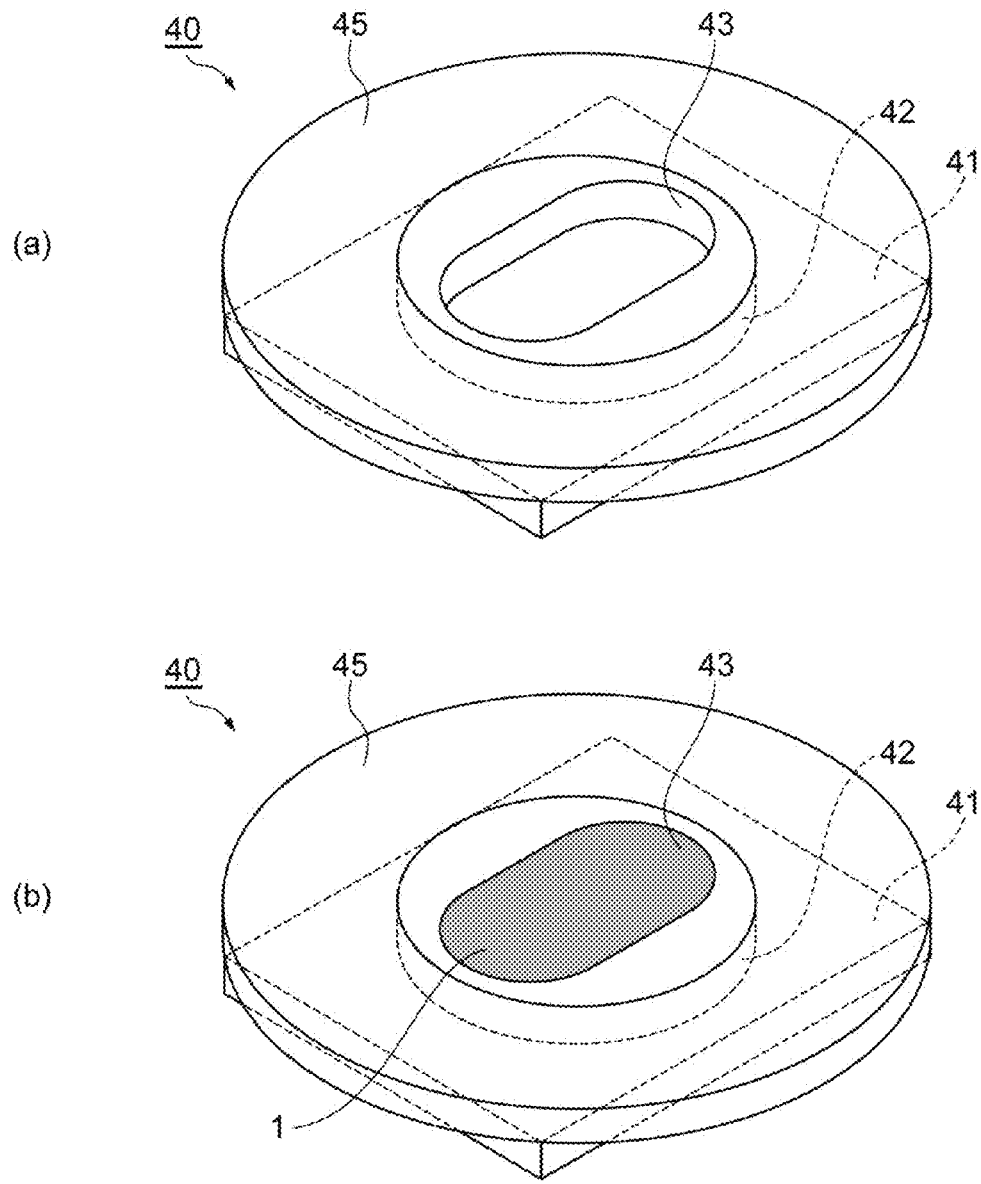
FIG. 8 includes (a) a perspective view illustrating housing of a sample in a housing container, and (b) a perspective view showing a continuation from (a) in FIG. 7.
Figure 10:
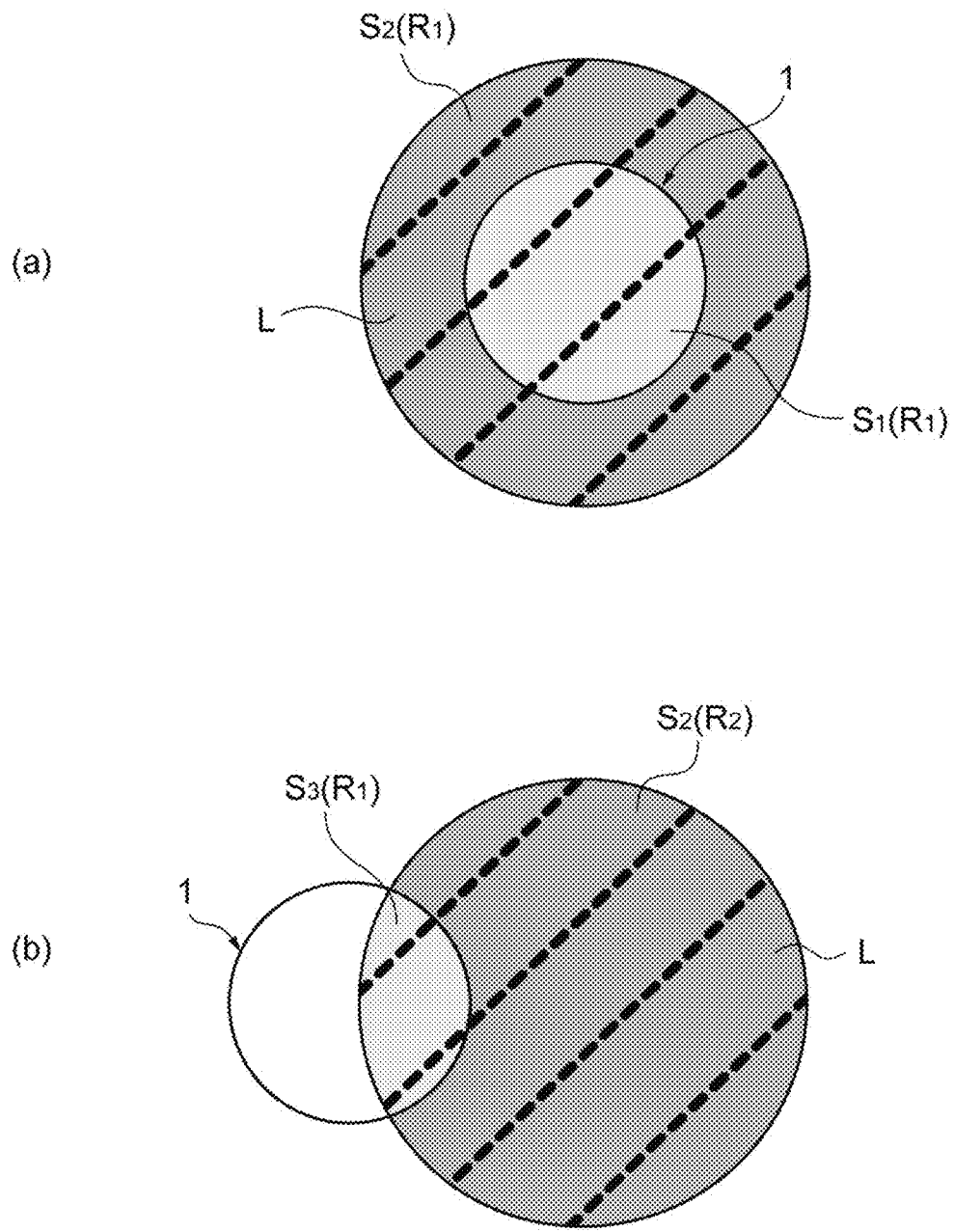
FIG. 10 includes (a) a schematic view showing an example of relationship between an irradiation area with excitation light and an irradiated area of a sample, and (b) a schematic view showing another example of relationship between the irradiation area with the excitation light and the irradiated area of the sample.

Thereafter, as shown in (b) in FIG. 8, the sample 1 is housed in the housing portion 43 of the sample container 40 with the housing aid cover 45 being attached thereto. Then the surface of the sample 1 is leveled with a metal brush or the like to flatten an exposed portion of the sample 1 and thereafter the housing aid cover 45 is detached from the sample container 40 with tweezers or the like. On the occasion of flattening the sample 1, an excess amount of the sample 1 is moved onto the housing aid cover 45, whereby the excess sample can be removed together with the housing aid cover 45 in the detaching process. This makes it feasible to prevent the sample 1 from adhering to the part other than the housing portion 43 of the sample container 40. In passing, if the sample container 40 is arranged in the integrating sphere 20 with the sample 1 adhering to the part other than the housing portion 43, the interior of the integrating sphere 20 will be contaminated thereby, raising a possibility of degradation of measurement accuracy.

Next, a sample cover (not shown) is mounted on the projected portion 42 of the sample container 40 and, as shown in FIGS. 4 and 5, the sample container 40 is arranged on the mount table 241 of the sample container holder 24 (S4). At this time, the sample container 40 is arranged in the four positioning portions 243 to be engaged with these positioning portions 243. This makes the sample container 40 positioned and fixed as directed in a predetermined direction, on the sample container holder 24; as a result, the long axis direction of the flange portion 41 of the sample container 40, the long axis direction of the housing portion 43, the long axis direction of the irradiation region $R_2$ with the excitation light L, and the inclination direction K1 of the mount table 241 (the inclination direction K2 of the housing portion 43) become aligned along the same direction.

Next, the sample container holder 24 with the sample container 40 thereon is attached to the sample introduction opening portion 23 (S5). Then sample measurement is performed which is spectral measurement in a state in which the sample 1 is arranged in the integrating sphere 20 (S6).

Specifically, the light is emitted from the excitation light source 11 and the excitation light L is guided through the input light guide 12 to be input from the input opening portion 21 into the integrating sphere 20, whereby the excitation light L is applied onto the sample 1 on the sample container holder 24. At this time, the excitation light L travels through the collimator lens and passes through the aperture 213, whereby the excitation light propagates as expanding in the integrating sphere 20, to be applied in the rectangular shape onto the sample 1. As a result, as shown in FIG. 5, the excitation light L is applied so as to include the sample 1.

The aperture 213 preferably has an opening of a shape having a long axis. Examples of the shape having the long axis include an elliptical shape, a rectangular shape, and so on. At this time, the long axis direction of the opening of the aperture 213 becomes identical to the long axis direction of the orthogonal plane to the irradiation optical axis of the excitation light L. Therefore, the long axis direction of the opening of the aperture 213 and the inclination direction K2 (long axis direction) of the housing portion 43 of the sample container 40 intersect at the angle with each other.

Thereafter, the light to be measured, after multiple diffuse reflections inside the integrating sphere 20, is guided from the output opening portion 22 through the output light guide 125 to the spectral analysis device 30 and the spectral analysis device 30 acquires a wavelength spectrum 15*b* (cf. (b) in FIG. 9). The light to be measured herein includes luminescence such as fluorescence generated in the sample 1 in response to the irradiation with the excitation light L, and components of light resulting from scattering, reflection, etc. by the sample 1 out of the excitation light L.

Then, the data analysis device 50 integrates the intensity in the excitation wavelength region in the wavelength spectrum 15*b* to acquire an excitation light region intensity Lb, and also integrates the intensity in a fluorescence wavelength region to acquire a fluorescence region intensity Lc. The excitation light region intensity Lb is obtained as an intensity reduced by a degree of absorption of the excitation light L by the sample 1, and the fluorescence region intensity Lc indicates an amount of fluorescence generated from the sample 1.

Then, the data analysis device 50 calculates the quantum yield, based on the acquired intensities La, Lb, and Lc (S7). Since the quantum yield is represented by a ratio of the number of photons of the light generated from the sample 1 and the number of photons of the excitation light L absorbed by the sample 1, it can be calculated as "external quantum efficiency of the sample 1 (the amount of the fluorescence emitted from the sample 1)"/"light absorptance of the sample 1 (the amount of the excitation light absorbed by the sample 1)." Therefore, for example, above S7 is to calculate the light absorptance based on a difference between the excitation light region intensities La, Lb and divide the external quantum efficiency on the fluorescence region intensity Lc by the light absorptance, to obtain the quantum yield. Finally, the analysis result is displayed on the display device 62, ending the measurement.

Here, in the above operation in the present embodiment, the wavelength spectra 15*a*, 15*b* can be subjected to apparatus correction with respect to measurement characteristics, detection sensitivity, etc. in the whole of the spectral measurement apparatus 100A. An apparatus correction coefficient to be used in the apparatus correction can be, for example, determined in advance and stored in the data analysis device 50. This makes it feasible to suitably take influence of the spectral measurement apparatus 100A itself into consideration in the spectral measurement of the sample 1.

Further, in the above operation in the present embodiment, the wavelength spectra 15a, 15b can be subjected to container correction with respect to absorption of light by the sample container 40. A container correction coefficient to be used in the container correction can be, for example, calculated through execution of reference measurement and sample measurement with use of white light, separately from the spectral measurement of the sample 1 (the foregoing S2, S6). This makes it feasible to suitably take influence of absorption of light by the sample container 40 into consideration in the spectral measurement of the sample 1.

Here, when the sample 1 is excited, fluorescence is emitted into all directions and many samples 1 have the absorption wavelength region also including the light of fluorescence wavelengths; therefore, the sample causes self-absorption such that the fluorescence generated by the sample 1 is absorbed by the sample 1 itself. For this reason, there is concern that the quantum yield is estimated smaller due to the self-absorption.

In this regard, the present embodiment can reduce the self-absorption amount for the following reason and thus can accurately determine the quantum yield. Namely, the reason is as follows: when the excitation light L is applied to a part of the sample 1, the self-absorption amount is large because of a large boundary area between the irradiated region and non-irradiated region in the sample 1; whereas in the present embodiment the excitation light L is applied so as to include the whole of the sample 1 and thus the boundary area between an irradiated region and a non-irradiated region in the sample 1 becomes smaller, so as to reduce the self-absorption amount.

Further, for example, when an ordinary laboratory dish is used as the sample container for housing the sample 1, the amount of the sample 1 needed is large and the self-absorption amount tends to increase because the excitation light L is applied to a part of the sample 1. In contrast to it, the sample container 40 in the present embodiment can house a small amount of the sample 1 and apply the excitation light L so as to enclose the whole of the sample 1, and for this reason, it becomes feasible to accurately measure the quantum yield even with the sample 1 in a small amount. Namely, the present embodiment enables the measurement with a small amount of sample as well, in the quantum yield measurement using the integrating sphere 20.

In the case of the ordinary laboratory dish being used, the amount of the sample 1 housed tends to vary depending upon users, but the use of the sample container 40 in the present embodiment allows us to make the amount of sample 1 constant, thereby facilitating comparison of measurement data of different samples 1. In passing, it can also be contemplated in the case of measuring a small amount of the sample 1 that the depth of the housing portion 43 is decreased, but in this case the sample 1 becomes more likely to be scattered than in use of the sample container 40; therefore, it is not practical, at least, in terms of usability.

Generally, the operation in the quantum yield measurement is based on the premise that the irradiation area $S_2$ with the excitation light L is smaller than the area of the sample 1, without assuming the condition that the area of the sample 1 is smaller than the irradiation area $S_2$ with the excitation light L. However, the quantum yield is calculated as relative value, as described above, and thus influence of the area of the sample 1 and the irradiation area $S_2$ can be cancelled; therefore, it can be said that the present embodiment also allows the quantum yield to be accurately determined, on the foregoing premise.

In the present embodiment, as described above, the sample container 40 is configured so as to be inclined relative to the perpendicular plane to the irradiation optical axis. This can prevent the excitation light L input through the input opening portion 21 into the integrating sphere 20 from being reflected by the sample 1 so as to be output from the input opening portion 21. As a result, the light to be measured from the sample 1 and the excitation light L reflected by the sample 1 can be actively multiply reflected in the integrating sphere 20, permitting more accurate measurement of quantum yield.

In the present embodiment, as described above, the housing aid cover 45 is used in the process of housing the sample 1 in the housing portion 43, whereby it can prevent the sample 1 from adhering to the flange portion 41 and inhibit the sample 1 from adhering to the high diffuse reflection material as the coating on the inner wall of the integrating sphere 20 and the sample container holder 24. In addition, since the long axis of the housing portion 43 of the sample container 40 is identical to the long axis of the flange portion 41, the direction of the housing portion 43 can be uniquely determined in the process of attaching the sample container 40.

In the present embodiment there are no particular restrictions on the position of the output opening portion 22 of the integrating sphere main body 200, but it may be located at any position, for example, where the light to be measured from the sample 1 is not directly incident thereto.

In passing, the present embodiment may be further provided with a lens to expand the excitation light L form the light output portion 7 so that the excitation light L includes the sample 1. In addition, the present embodiment has the collimator lens 212 and the aperture 213 as the incidence optical system but may be equipped with only either one of them. Furthermore, since the expanded excitation light L is output from the input light guide 12, the incidence optical system may be configured including the output end of the input light guide 12 (or composed of it only).

Figure 11:
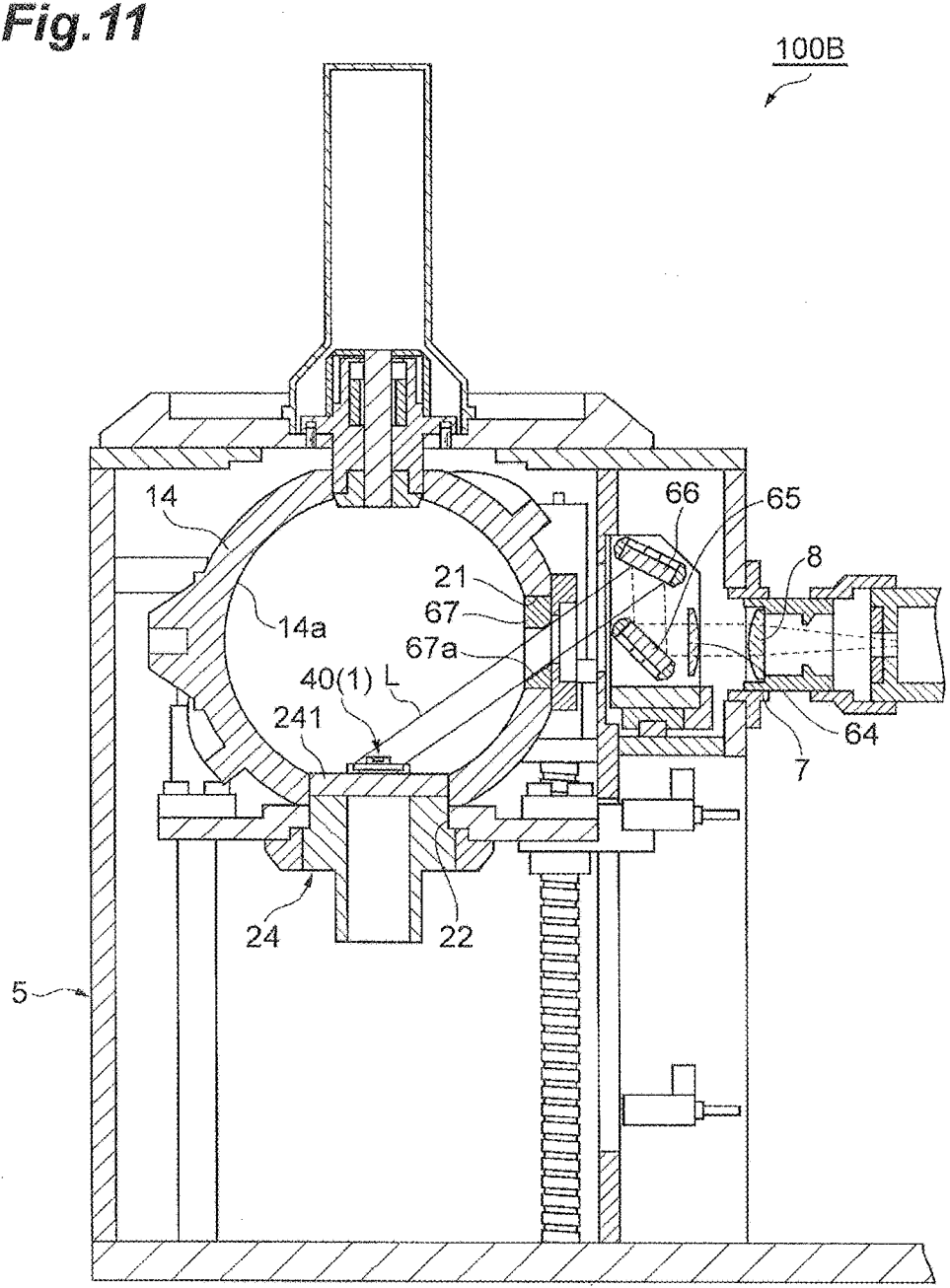
FIG. 11 is a cross-sectional view showing a spectral measurement apparatus according to a modification example.

FIG. 11 is a cross-sectional view showing the spectral measurement apparatus according to a modification example. As shown in FIG. 11, the spectral measurement apparatus 100B of the modification example has a configuration wherein the excitation light L can be applied obliquely to the sample 1. The spectral measurement apparatus 100B of this configuration has a dark box 5.

The dark box 5 is a box of a rectangular parallelepiped shape made of metal and blocks entrance of light from the outside. An inner surface 5a of the dark box 5 is provided with a coating or the like of a material that absorbs the excitation light L and the light to be measured. An integrating sphere 14 is arranged in the dark box 5. The integrating sphere 14 is provided with a coating of a high diffuse reflection agent such as barium sulfate on its inner surface 14a or is made of a material such as PTFE or Spectralon. A light detection unit (not shown, a photodetector) is connected through an output opening portion to this integrating sphere 14.

A light output portion 7 of a light generation unit (not shown) is connected to one side wall of the dark box 5. The light generation unit is an excitation light source, for example, configured by a xenon lamp, a spectroscope, and so on, and generates the excitation light L. The excitation light L is collimated by a lens 8 provided at the light output portion 7, to be input into the dark box 5.

Between the lens 8 and the integrating sphere 14 in the dark box 5, there are a collimator lens 64 and mirrors 65, 66 disposed in this order from the upstream to downstream on the irradiation optical axis. An aperture 67 is provided at an input opening portion 21 of the integrating sphere 14. The aperture 67 has an opening portion of a shape having a long axis and a cut portion 67a is formed in at least a part of the opening portion of the aperture 67. The shape of the cut portion 67a is made so that the excitation light L passing through the aperture 67 to impinge upon the sample 1 becomes wider than a region of the sample 1 (the area of the sample 1 on a top plan view).

These collimator lens 64, mirrors 65, 66, and aperture 67 constitute an incidence optical system for making the excitation light L incident to the sample 1. In this incidence optical system, the excitation light L input into the dark box 5 is collimated by the collimator lens 64, successively reflected by the mirrors 65, 66, and guided through the aperture 67 into the integrating sphere 14, whereby the excitation light L is applied to the sample container 40 so as to include the sample 1 in the integrating sphere 14. The mirror 66 is an optical member for adjusting the angle of incidence of the irradiation optical axis of the excitation light L so as to incline an orthogonal plane (perpendicular plane) to the irradiation optical axis of the excitation light L, relative to the opening plane 43a of the housing portion 43 of the sample container 40. This makes the inclination direction of the opening plane 43a of the housing portion 43 relative to the orthogonal plane to the irradiation optical axis of the excitation light L, identical to the long axis direction L1 (cf. FIG. 3) of the opening plane 43a of the housing portion 43.

The spectral measurement apparatus 100B of the modification example may be provided with a lens for expanding the excitation light L from the light output portion 7 so that the excitation light L includes the sample 1. The apparatus is equipped with the collimator lens 64, mirrors 65, 66, and aperture 67 as the incidence optical system but it may be modified so as to be equipped with the aperture 67 only. Furthermore, since the expanded excitation light L is output from the light output portion 7, the incidence optical system may be configured including the output end of the light output portion 7 (or may be composed of it only).

The above described the preferred embodiment but it should be noted that the present invention is by no means intended to be limited to the above embodiment but may be modified without change in the spirit and scope of the invention as described in each of the claims, or may be applied to others.

For example, the above embodiment used the integrating sphere 14 as an integrator, but the integrator may be any means (optical component) for spatially integrating light inside it; for example, the integrating hemisphere disclosed in Japanese Patent Application Laid-Open No. 2009-103654 may be adopted. In addition, the above embodiment needs only to be configured so that the excitation light L includes the sample 1; for example, it may be configured so that the excitation light L includes the sample 1, by adjusting at least one of the incidence optical system of the excitation light L and the shape of the housing portion 43 of the sample container 40.

In the above embodiment the sample container holder 24 as a sample holder attached to the integrator held the sample container 40 having the housing portion 43, but the sample container holder 24 having the housing portion 43 may be attached to the integrator.

The above embodiment mainly showed the quantum yield (efficiency) measurement as an object of the spectral measurement apparatus and spectral measurement method, but, without having to be limited to it, the object may be reflectance measurement or transmittance measurement or the like.

INDUSTRIAL APPLICABILITY

The one aspect of the present invention has made it feasible to accurately determine the quantum yield.

REFERENCE SIGNS LIST

1—sample, 11—excitation light source (light source), 14, 20—integrator, 21—input opening portion, 22—output opening portion, 23—sample introduction opening portion, 24—sample container holder (sample holder), 31b—photodetector, 40—sample container, 41—plate portion (flange portion), 42—projected portion, 43—housing portion, 43a—opening plane, 50—data analysis device (analysis means), 64—collimator lens (incidence optical system), 65, 66—mirror (incidence optical system), 67—aperture (incidence optical system), 100A, 100B—spectral measurement apparatus, 212—collimator lens (incidence optical system), 213—aperture (incidence optical system, optical member), 241—mount table (inclined member), L—excitation light.

The invention claimed is:

1. A spectral measurement apparatus for irradiating a sample as a measurement object with excitation light and detecting light to be measured, comprising:
    a light source configured to generate the excitation light;
    an integrator having an input opening portion for inputting the excitation light, and an output opening portion for outputting the light to be measured;
    a sample container made of a transparent material and including a housing portion defining a depressed portion for housing the sample and arranged in the integrator;
    an incidence optical system configured to irradiate the sample with the excitation light so that an irradiation area of the excitation light is set larger than an opening area of the depressed portion and the sample in the depressed portion;
    a photodetector configured to detect the light to be measured output from the output opening portion and to output a detection signal; and
    an analyzer configured to calculate a quantum yield of the sample, based on the detection signal.

2. The spectral measurement apparatus according to claim 1, wherein the integrator has a sample introduction opening portion for attaching, a sample holder for arranging the sample container, and wherein
    the sample holder is attached to the sample introduction opening portion so that an opening plane of the housing portion is inclined relative to an orthogonal plane to an irradiation optical axis of the excitation light.

3. The spectral measurement apparatus according to claim 2, wherein an inclination direction of the opening plane of the housing portion and a tong axis direction of the opening plane of the housing portion are identical to each other.

4. The spectral measurement apparatus according to claim 2, wherein the incidence optical system comprises an optical member including an opening having a long axis, and wherein there is an angle between a long axis direction of the opening of the optical member and an inclination direction of the opening plane of the housing portion.

5. The spectral measurement apparatus according to claim 2, wherein the sample holder has a mount surface for the sample container to be mounted thereon, and is attached to the sample introduction opening portion so that the mount surface is inclined relative to the orthogonal plane to the irradiation optical axis of the excitation light.

6. The spectral measurement apparatus according to claim 5, wherein the sample holder comprises an inclined member having the mount surface.

7. The spectral measurement apparatus according to claim 2, wherein the incidence optical system has an optical member for adjusting an angle of the irradiation optical axis to the opening plane of the housing portion.

8. A spectral measurement method for irradiating a sample as a measurement object with excitation light and detecting light to be measured, comprising:

arranging the sample in an integrator having an input opening portion for inputting the excitation light, and an output opening portion for outputting the light to be measured, in a state in which the sample is housed in a housing portion of a sample container made of a transparent material, the housing portion defining a depressed portion for housing the sample;

irradiating the sample with the excitation light so that an irradiation area of the excitation light is set larger than an opening area of the depressed portion and the the sample in the depressed portion;

detecting, by a photodetector, the light to be measured output from the output opening portion of the integrator and outputting a detection signal; and calculating a quantum yield of the sample, based on the detection signal.

* * * * *